United States Patent [19]

Hatton et al.

[11] Patent Number: 4,662,749
[45] Date of Patent: May 5, 1987

[54] FIBER OPTIC PROBE AND SYSTEM FOR PARTICLE SIZE AND VELOCITY MEASUREMENT

[75] Inventors: T. Alan Hatton, Cambridge; Joel L. Plawsky, Boston, both of Mass.

[73] Assignee: Massachusetts Institute of Technology, Cambridge, Mass.

[21] Appl. No.: 796,646

[22] Filed: Nov. 8, 1985

[51] Int. Cl.$^4$ ............................................. G01N 21/51
[52] U.S. Cl. .................................. 356/336; 250/227; 250/574; 356/338
[58] Field of Search ............... 356/335, 336, 338, 341, 356/343; 250/227, 564, 573, 574

[56] References Cited

U.S. PATENT DOCUMENTS

| | | | |
|---|---|---|---|
| 3,906,241 | 9/1975 | Thompson | 250/574 |
| 3,954,342 | 5/1976 | Boeke | 250/565 X |
| 4,497,577 | 2/1985 | Sato et al. | 356/343 X |
| 4,595,291 | 6/1986 | Tatsuno | 356/336 |

OTHER PUBLICATIONS

"An Instrument for Spray Droplet Size & Velocity Measurements", W. D. Bachalo, et al., Paper No. 79--WA/GT-13, *ASME* vol. 102, Oct. 1980.
"Phase/Doppler Spray Analyzer for Simultaneous Measurements of Drop Size & Velocity Distributions", W. D. Bachalo, & M. J. Houser Optical Engineering, Sep./Oct., 1984, vol. 23, No. 5.
"Fringe Image Technique for the Measurement of Flow Velocities" E. A. Ballik & J. H. C. Chan, *Applied Optics*, Nov. 1973, vol. 12, No. 11.
"Simultaneous Measurement of Size & Velocity of Bubble or Drops: An New Optical Technique", Raphael Semiat & A. E. Dukler, *AIChE Journal*, vol. 27, No. 1, Jan., 1981.
"Instrument for Velocity & Size Measurement of Large Particles", Gabriel Laufer, *Applied Optics*, vol. 23, No. 8, Apr. 15, 1984.
"Fiber-optic Lawer Doppler Anemometer with Bragg Frequency Shift Utilising Polarisation-Preserving Single-Mode Fiber" by Knuhtsen et al. *J. Phys. E. Sci. Instrum.*, vol. 15; 1982 printed in Gr. Britain.

*Primary Examiner*—Davis L. Willis
*Assistant Examiner*—Matthew W. Koren
*Attorney, Agent, or Firm*—Hamilton, Brook, Smith & Reynolds

[57] ABSTRACT

A system for the simultaneous measurement of the size and velocities of bubbles or drops in a multiphase process environment wherein light passing through a Ronchi grating is projected onto a measurement volume within the multiphase process stream by a coherent fiber optic bundle and a gradient index imaging lens. Drops or bubbles passing through the measurement volume reflect or refract light which is sensed by velocity and size sensor fiber optic bundles disposed opposite the imaging lens and the sensed signal is coupled to signal processing means which convert the light signal to electrical signals and the appropriate size velocity measurements are made using one or more of the visibility techniques, phase lag techniques or transit time techniques.

9 Claims, 10 Drawing Figures

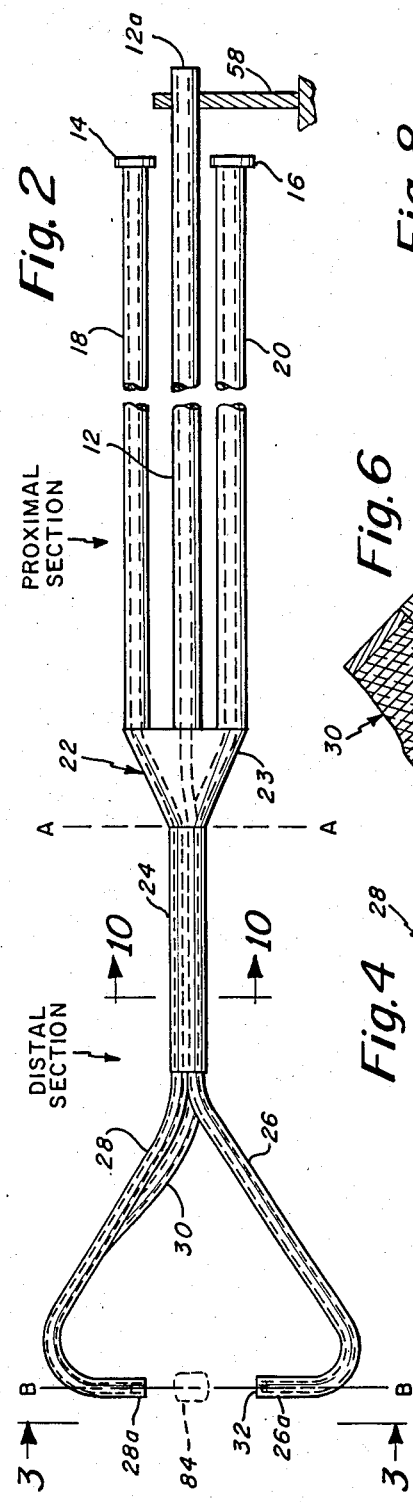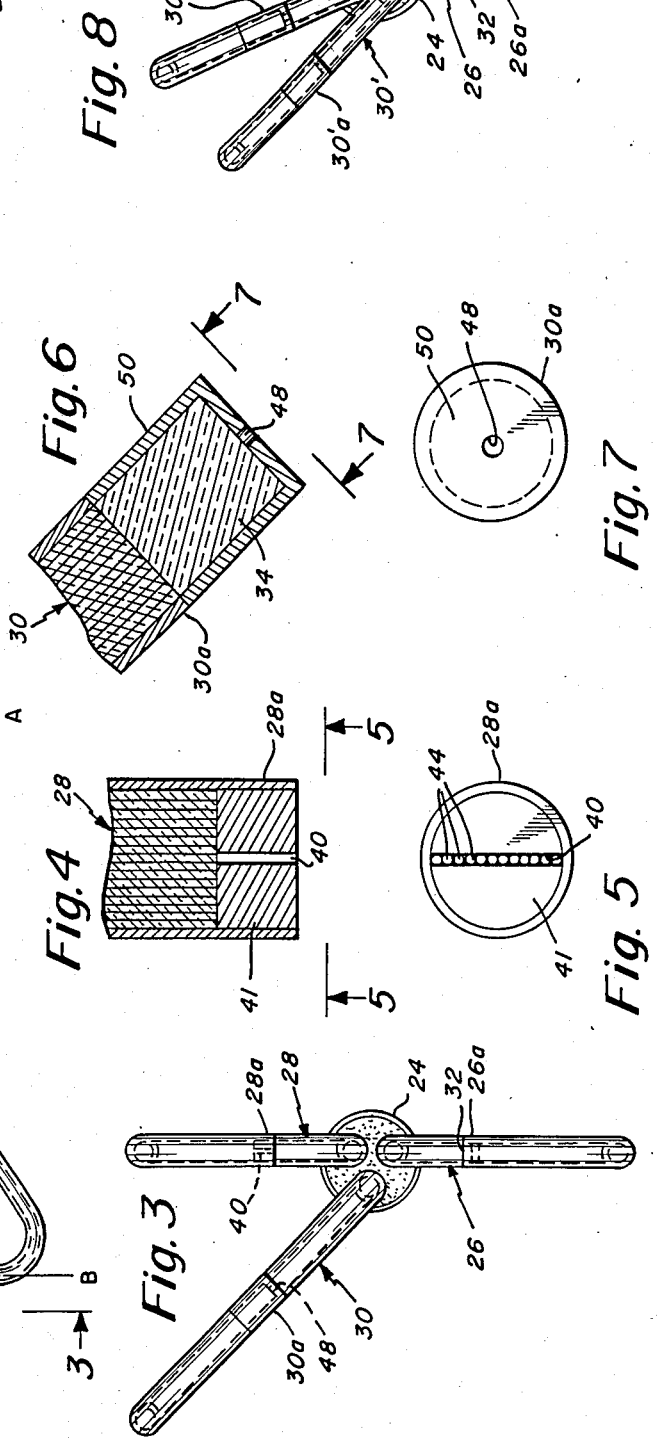

FIBER OPTIC PROBE AND SYSTEM FOR PARTICLE SIZE AND VELOCITY MEASUREMENT

The Government has rights in this invention pursuant to Grant Number NSF CPE 8413859 awarded by the National Science Foundtion.

TECHNICAL FIELD

This invention relates to apparatus for measuring the size and velocity of particles, such as bubbles or drops, in dispersed multi-phase mediums.

BACKGROUND ART

Information concerning the size and velocity of particles in a dispersed multi-phase medium is essential for accurate modelling and design of certain industrially important equipment. Such equipment includes, for example, spray absorbers, bubble columns, pipeline reactors and other contacting equipment.

Laser Doppler techniques for single phase velocity measurements have been available for about 20 years. Such techniques utilize the frequency of the light scattered by micron sized particles passing through a measurement volume defined by the intersection of two coherent laser beams to determine particle velocity. More recently, systems have been developed to also extract particle size information from the light scattered signal using the visibility technique (Bachalo et al., "An Instrument for Spray Droplet Size and Velocity Measurements", *Engineering for Power*, Vol. 102, No. 4, October 1980), or the phase lag approach (Bachalo et al., "Phase/Doppler Spray Analyzer for Simultaneous Measurements of Drop Size and Velocity Distributions", *Optical Engineering*, Vol. 23, No. 5, September-/October 1984).

In the visibility method of particle size measurement, the AC and Pedestal components of the Doppler signal generated by a particle passing through the crossed laser beams are separated. The ratio of the areas under the AC and Pedestal curves is proportional to particle size.

Crossed or referenced coherent laser techniques of the Bachalo et al. type depend upon the so-called Mie scattering phenomenon and, consequently, are most useful for particles below 150 microns in diameter. In response to the need for instruments which would measure larger particle sizes, an alternate technique was developed.

This alternative technique, first introduced by Ballik and Chan ("Fringe Image Technique for the Measurement of Flow Velocities", *Applied Optics*, Vol. 12, No. 11, November 1973) uses a single incoherent light beam passed through a Ronchi grating to generate the requisite fringes required for the Doppler technique. Semiat and Dukler ("Simultaneous Measurement of Size and Velocity of Bubbles or Drops: A New Optical Technique", *AIChE Journal*, Vol. 27, No. 1, January 1981) applied this Ronchi grating technique to the joint measurement of drop size/velocity distributions in dispersed phase processes. Semiat and Dukler use a transit time technique to measure drop size.

In the transit time size measurement technique, drops transversing a series of light and dark fringes generated by passing a laser beam through a Ronchi grating refract or reflect light which is collected by receiving optics. The frequency spectrum of the collected signal is used to measure particle velocity while the duration ("transit-time") of the decrease in beam intensity caused by blockage of the beam as particles pass through the fringes is used to measure particle size.

All of these prior art techniques are feasible in theory but suffer from certain practical disadvantages in practical implementation. A principal disadvantage results from the manner in which the grating images or cross laser beam patterns are imaged into the two-phase medium under measurement. In normal practice, the medium is enclosed in an opaque walled column or vessel. A viewing window is provided on a wall of the column or vessel and the crossed laser beams or fringe images are projected into the medium. In many applications, the depth of penetration is very limited due to the density of the dispersed medium. Thus, local measurements of particle size/velocity throughout a cross-section of the medium become difficult or impossible. Furthermore, it is difficult to maintain a stable focussed small volume fringe image within the medium from the relatively remote walls of the column or vessel. Furthermore, to project this image throughout different crosssections of the medium necessitates extensive time consuming and laborious realignment of the optical projecting system.

DISCLOSURE OF THE INVENTION

The above disadvantages and/or restrictions of the prior art systems may be resolved or overcome, in accordance with the present invention. The apparatus of the present invention comprises, in general, an optical light projecting assembly for projecting a fringe image consisting of a series of parallel planes of alternating dark and light spaces; and a probe consisting of (i) a transmitting coherent fiber bundle having a proximal end near the light projecting assembly and a distal end projecting into the multi-phase medium for transferring the fringe image from the proximal to the distal end thereof, (ii) a lens for projecting the transferred fringe image into a measurement zone within the medium, and (iii) receiving fiber optic bundles having a distal end adjacent the lens for collecting light reflected or refracted from particles, i.e., bubbles or drops, passing through the measurement zone and transferring said light to the proximal end thereof; and signal processing apparatus for converting the received light to an electrical signal corresponding to the frequency, phase and amplitude components of the received light and calculating the velocity and/or size of the particles therefrom, in accordance with the visibility technique, travel time technique or both.

Preferably, the distal end of the coherent fiber bundle and receiving fiber optic bundles projecting into the medium are enclosed in a rigid sleeve.

Among the advantages of the apparatus of the invention are the following:

(i) Unlike the crossed laser techniques, a coherent light source is not needed.

(ii) By focussing only the fundamental Fourier fringe images directly from the grating onto the probe, many of the problems inherent in the Semiat and Dukler approach are avoided. The clarity of the grating image is retained, and the appearance of additional harmonic components of the fundamental grafting frequency, due to Fresnel diffraction effects, do not arise. (iii) Dense dispersions can be penetrated with minimal flow disturbance since the rigid distal portion of the probe is relatively small in diameter. Thus, it now becomes possible to measure local dispersed-phase properties at points far removed from the vessel or column wall.

(iv) The light source can be sited remotely from the experimental apparatus, optical coupling between the light source and measurement volume being via a flexible coherent fiber bundle (Imagescope). This significantly reduces problems associated with vibrations, etc., in the system.

(v) Movement of the probe within the flow system is possible without the need for optics realignment or adjustment, since all the optics are mounted externally together with the light source, and are coupled flexibly with the probe via the imagescope and flexible fiber optic receiving sensors.

(vi) The measurement volume is well-defined and small. For wide fringe spacings in conventional Laser Doppler Anemometers systems, the subtended angle between the two crossed beams must be small, and this leads to a large, elongated measurement volume.

(vii) The remote siting of the optical light projecting assembly and the rigid qualities of the inserted distal probe construction permits implementation of this measurement technique in many hostile industrial settings.

These advantages and other details of the invention will now be explained in connection with the drawings.

BRIEF DESCRIPTION OF THE DRAWINGS

FIG. 2 is a partially sectionalized view of the probe 10 of the invention.

FIG. 3 is an end view taken along lines 3—3 of the distal end of the probe 10 of the invention.

FIG. 4 is an enlarged sectional view of the slot receptor portion 28a of the receiver optics.

FIG. 5 is an end view taken along the lines 5—5 of the slot receptor 28a of FIG. 4.

FIG. 6 is an enlarged cross-sectional view of the velocity receptor portion 30a of the receiver optic portion of the probe 10.

FIG. 7 is an end view taken along the lines 7—7 of FIG. 6.

FIG. 8 is an end view of an alternate embodiment of a probe wherein the velocity receptor is subdivided into two adjacent receptor assemblies thereby enabling drop size to be measured using a phase lag technique.

BEST MODE OF CARRYING OUT THE INVENTION

I. The System

Figure 1:
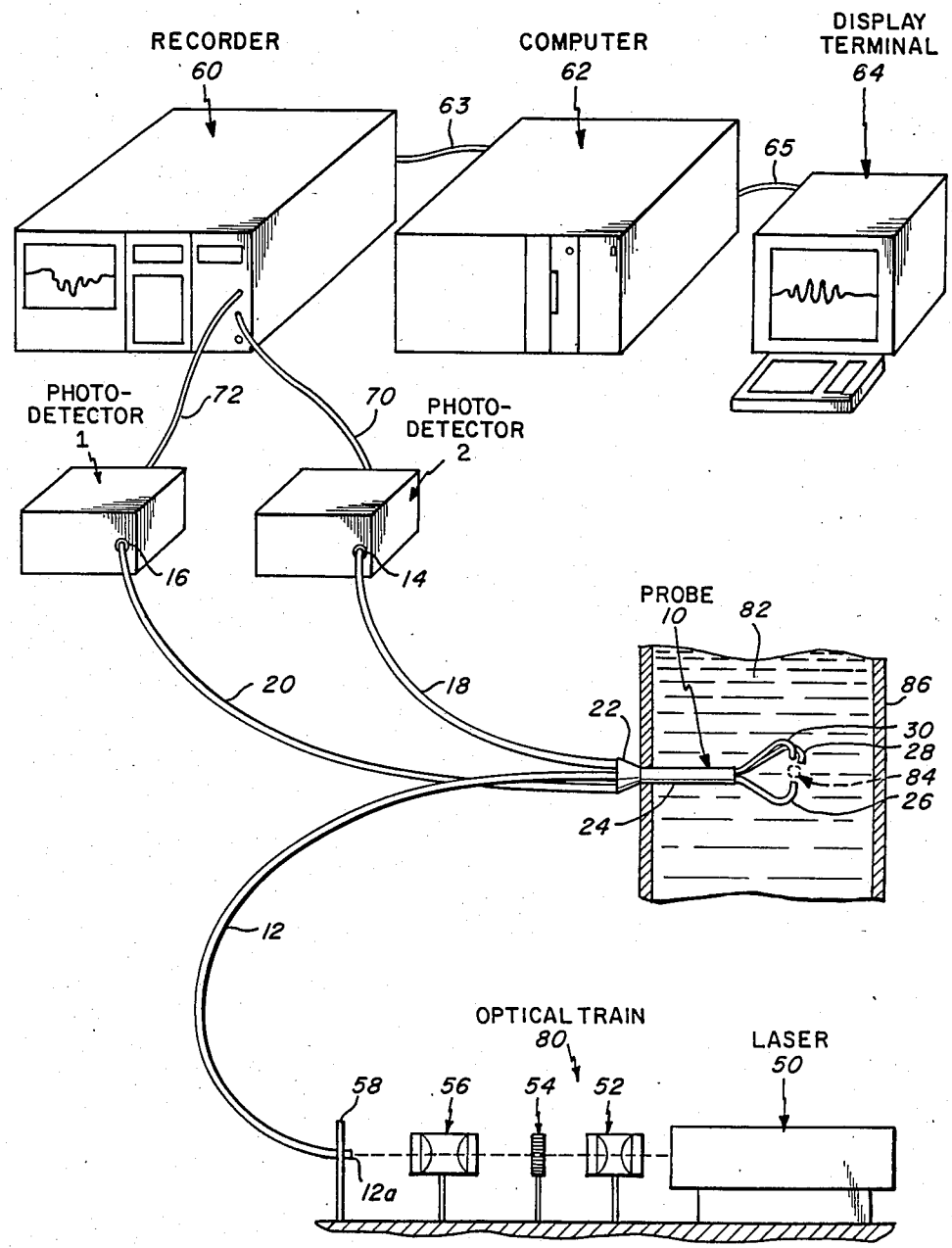
FIG. 1 is a block diagram of the overall system of the invention.

FIG. 1 shows the overall system of the invention in block diagram form. As may be seen therein, the system comprises a first optical light projecting assembly or optical train 80 which includes a laser 50 for projecting a beam of light, shown in dotted lines, through a collimating lens system 52.

The collimated light beam is projected through a grating 54, such as a Ronchi grating. The Ronchi grating consists of a glass or plastic substrate upon which a series of light and dark lines are ruled or engraved. Any light, even non-coherent white light, passed through the Ronchi grating, produces a continuous series of parallel planes of alternating dark and light spaces on the other side of the grating 54.

An imaging lens 56 is provided adjacent the Ronchi grating 54 to image the alternating dark and light spaces (fringes) onto the proximal end 12a of a flexible imagescope 12. The proximal end 12a has an optically polished surface held in alignment by support 58 with the projected fringe image from lens 56.

Imagescope 12 consists of a coherent fiber optic bundle 12 in which the proximal and distal ends of the fibers in the bundle are arranged in the same spatial relative position at both ends. Thus, despite any twisting or dislocation of the flexible fiber bundle 12, an image at the proximal end 58 will be transferred or transmitted to the distal end in the same relative image relationship, as it appeared at the proximal end.

The transmitting imagescope or coherent fiber optic bundle 12 extends into probe 10 through transition member 22 and extends through a vessel or column wall 86 containing a dispersed multi-phase medium 82 which contains flowing particles, such as bubbles or drops, the size and velocity of which are desired to be measured.

The details of probe 10 will be described in detail in connection with FIG. 2. For the present, it should be noted that in addition to the transmitting coherent fiber optic bundle 12, probe 10 includes the transition member 22 and a pair of receiving fiber optic bundles 30 and 28, one of which (28) incorporates a slot receptor for size and velocity measurement using the transit time technique, the other of which (30) comprises a velocity receptor for measuring velocity using the frequency technique. All three fiber optic bundles, 30, 28 and 26, are substantially enclosed in a metallic rigid sheath 24 to enable the probe 10 to be conveniently inserted into the medium 82 and yet remain relatively protected from the environment. A small measurement zone 84 is formed or defined between the distal ends of the fiber optic bundles 26, 28 and 30. The proximal ends of the fiber optic receiving bundles 30 and 28, pass through the sheath 24 through the transition member 22.

The proximal end 18 of fiber optic bundle 28 is coupled to photodetector 2 via connector 14 while the proximal end 20 of fiber optic bundle 30 is coupled to photodetector 1 via connector 16 wherein the light sensed at the proximal ends of the bundles is converted or transformed to an electrical signal porportional to the frequency amplitude and phase of the sensed light. The photodetectors 1 and 2 are coupled via respective cables 72 and 70 to the input terminals of recorder 60 wherein the sensed electrical waveforms are recorded for future use. Computer means 62 is coupled via cable 63 to recorder 60, and is programmed to calculate the size and velocity of particles passing through the measurement zone 84 in accordance with well known techniques described in the references cited in the Background Art. Such size and velocity information, as calculated by the computer, may be conveniently displayed on display terminal 64 which is coupled to computer 62 via leads 65.

II. The Probe

Referring now to FIGS. 2-7, the probe 10 will be described in detail. Probe 10 consists of a proximal section, shown generally on one side of dotted line A—A and a distal section on the opposite side of line A—A. The distal section is adapted to be inserted into the multiphase medium through the walls of the vessel or column; while the proximal section of the probe consists of relatively flexible fiber optic bundles 12, 18 and 20. These bundles are coupled, respectively, to imaging lens 56, photodetector 2 and photodetector 1, as shown in FIG. 1.

Connector 14, attached to fiber optic bundle 18, is used to connect the fiber optic bundle to photodetector 2. Connector 16 is used to connect the fiber optic bundle 20 to photodetector 1.

A transition member 22, comprising an outer plastic enclosure 23, adapted to be mounted on the wall of a column or vessel, accepts the fiber optic bundles 10, 12 and 18 and feeds them into a rigid metal sheath 24 adapted to be inserted into the medium through openings provided in the wall or vessel.

Figure 10:
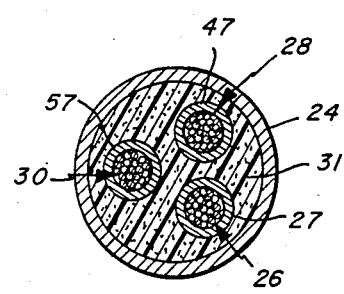
FIG. 10 is a cross-sectional view taken along the lines 10—10 of FIG. 2 showing the details of the metal sheath.

FIG. 10 is a cross-sectional view along the lines 10—10 showing the details of the metal sheath 24, the bundles 26, 28 and 30, each surrounded by protective metal sheaths or conduits 27, 47 and 57, respectively. All of these bundles are potted in place by epoxy 31.

The distal ends of the three fiber optic bundles, 18, 12 and 20, extend beyond the metal sheath 24 and are shown, respectively, as items 28, 26 and 30. As may be seen in FIGS. 2 and 3, the distal ends of the fiber optic conduits 26, 28 and 30 are bent into a cone-shape, such that the transmitting coherent fiber optic bundle 26 is disposed opposite the distal end 28a of fiber optic bundle 28, while the distal end 30a of receiving fiber optic bundle 30 is disposed at an askew angle of about 45° with respect to the distal ends of the other two fiber optic bundles.

Figure 9:
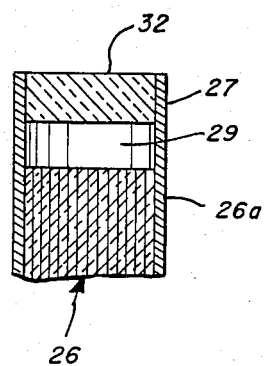
FIG. 9 is an enlarged view of the end portion of the distal end of a transmitting optic bundle in accordance with the invention.

FIG. 9 is an enlarged view of the end portion of the distal end 26a of the transmitting optic bundle showing the lens 32 in place between a metal sheath 27 extending along the length of the bundle. A small gap 29 is formed between the line 27 and the coherent fiber bundle 29 to focus the fringe image a distance from the lens 27 surface.

The transmitting fiber optic bundle 26 has a gradient index lens 32 of small diameter (approximately 2 millimeters), formed or cemented to the polished ends of the fiber bundle. Lens 32, which is preferably a Selfoc-type imaging lens, forms an image of the fringe or grating pattern from the Ronchi grating 54 at a distance of about 1 centimeter from the distal surface of the lens 32, as shown at 84. Directly opposite lens 32 is the receiving fiber optic bundle 28, the distal end of which is shown in detail in FIGS. 4 and 5. As may be seen therein, the distal end of the fiber optic bundle 28a comprises a slot receptor in the form of a linear array or ribbon of fibers 44, approximately 2 millimeters wide, disposed in a 75 microns deep slot 40 formed in plug 41.

As a drop or bubble passes through the measurement zone 84, the intensity of the light impinging on the fiber optic ribbon diminishes. The duration of this interruption in signal intensity is directly related to the drop size and velocity. This change in light intensity signal is coupled via the fibers in fiber optic bundle 28 to the connector 14 at the proximal end and ultimately to photodetector 2 of FIG. 1.

A velocity receptor is formed on the distal end of fiber optic bundle 30. This velocity receptor or velocity signal detector, consists of a bundle of 50 micron fibers cemented to a 1 millimeter wide angle Selfoc grating index micro-lens 34 covered by a 300 micron diameter pinhole 48 in an opaque member 50. The velocity receptor is disposed at a predetermined angle about a sphere whose center is located on the center of the movement volume, such as 45°, to the optical axis B—B, passing through the center of the lens 32 and the measuring volume 84.

Depending upon which side of a plane perpendicular to axis B—B and passing through the center of the measured volume the velocity receptor is located, it will receive refracted or reflected light signals from drops or spots passing through the measurement volume 84. These light signals are then coupled via the fiber optic bundle 30 to externally located photodetector 1 via flexible fiber optic bundle 20 at the proximal end of probe 10. The frequency information in this detected signal is used to calculate the velocity of the drop or bubble while the relative AC to DC intensities of the signal are used to calculate the drop size via well-known visibility techniques, described in the prior art.

In the alternate embodiment, shown in FIG. 8, two velocity receptors 30'a and 30'b, along with appropriate fiber optic bundles are employed as receiving elements and are used to generate light intensity signals from drops passing through the measurement volume 84.

The two velocity receptors are displaced from each other by a short distance so that when the drop passes through the measurement volume 84, two signals are obtained which are separated in time, so that there is a slight phase difference between the two signals. This phase difference is dependent on the curvature of the drop surface, and therefore the size of the drop. The phase difference, as detected by the sensors are coupled to the proximal end, to determine the size of the drop by well-known means.

This completes the overall description of the invention. Experimental apparatus has been developed utilizing the concepts above described. In this apparatus, a coherent source of light was utilized comprising a 20 milliwatt helium neon laser. However, it should be emphasized that it is not necessary to utilize coherent light in the operation of the apparatus of the invention. Additionally, while Ronchi gratings have been used in the present device for generating fringe patterns, it is possible to generate them by other means. For example, crossed laser beams could be generated adjacent the imagescope to produce fringes which could be coupled to the lens 32 via imagescope 12 and imaged into the measurement zone.

The Ronchi grating may be formed on a disc of 10 centimeters in diameter with approximately 4000 radial lines corresponding to a fringe spacing of 20 lines per millimeter. The disc may be rotated to obtain frequency shifting of the velocity signal. Conventional electronic feedback controls may be utilized to control the rotational speed of the disc.

Equivalents

Those skilled in the art may recognize other equivalents to the specific embodiments described herein, which equivalents are intended to be encompassed by the claims attached hereto.

We claim:
1. A system for the simultaneous measurement of the size and velocity of particles within a multiphase process comprising:
 (a) a source of light for generating a light beam;
 (b) fringing means for projecting a fringe image of a series of parallel planes of alternating dark and light spaces in response to said light beam;

(c) imaging means having proximal and distal ends comprising a coherent fiber optic bundle for transmitting said fringe image from the proximal end of the imaging means to the distal end thereof;

(d) lens means at the distal end of the imaging means for projecting said fringe image into space;

(e) velocity and size sensor means comprising fiber optic means having a distal end located adjacent said lens means at an askew angle with respect to said lens means for sensing the light refracted or reflected from particles passing through the fringe image and for transmitting said reflected or refracted signal to the proximal end of said sensor means;

(f) light detector means coupled to the proximal end of said sensor means for converting the sensed light to an electrical signal proportional thereto; and (g) signal processing means for determining the velocity and size of said particles in response to said electrical signal.

2. The system of claim 1 wherein a substantial portion of the distal end of the imaging means, and the sensor means is sheathed in a rigid conduit.

3. The system of claim 1 including an additional sensor means comprising a plurality of optical fibers, the distal ends of which are laterally aligned in a plane through an axis extending from the center of the lens means and the center of the fringe image for detecting the intensity and duration of the change in light impinging on said additional sensor means, as particles pass through the fringe image.

4. A system for the simultaneous measurement of the size and velocity of bubbles or drops in a multiphase process comprising:

(a) a source of light for generating a light beam;

(b) fringing means for projecting a fringe image of a series of parallel planes of alternating dark and light spaces in response to said light beam;

(c) imaging means comprising a coherent fiber optic bundle for transmitting said fringe image from the proximal end of the imaging means to the distal end thereof;

(d) lens means at the distal end of the imaging means for projecting said fringe image into space, said space forming a measurement volume;

(e) first sensor means comprising first fiber optic means aligned opposite said first lens means for transmitting to the proximal end of said first sensor means a light intensity signal proportional to the size and velocity of drops or bubbles passing through said fringe image;

(f) second sensor means comprising second fiber optic means located at an askew angle with respect to said lens means for sensing the light intensity reflected or refracted from drops or bubbles passing through the fringe image for transmitting a second light intensity signal to the proximal end of said second sensor means;

(g) light detector means coupled to the proximal ends of said first and second sensor means for converting the first and second light intensity signals to electrical signals proportional thereto; and (h) signal processing means for determining the velocity and size of said drop or bubble in response to said light intensity signals.

5. The system of claim 4 wherein a substantial portion of the distal ends of the imaging means, and the first and second sensor means is sheathed in a rigid conduit.

6. The system of claim 4 wherein the fiber optic means of the first sensor means comprises a plurality of optical fibers laterally aligned in a plane through an axis extending from the center of the lens means to the center of the first sensor means.

7. A probe adapted to be partially inserted into a dispersive multi-phase medium wherein particles circulate in a wall enclosed stream for the measurement of particle size or velocity comprising:

(a) imaging means having a relatively rigid distal end projecting through said wall into said stream and a relatively flexible proximal end outside of said stream comprising a coherent fiber optic bundle for transmitting a fringe image consisting of a series of alternating dark and light spaces from the proximal end of said imaging means to the distal end thereof;

(b) lens means at the distal end of the imaging means for projecting said fringe image into a measurement space within the stream adjacent said lens means;

(c) fiber optic means having a distal end within the stream and a proximal end outside the stream and wherein the distal end is displaced from the distal end of the imaging means for sensing the light intensity of light reflected from particles passing through the fringe image and for coupling said light intensity to the proximal end thereof.

8. The probe of claim 7 further including a transit time sensor means for measuring particle size and velocity comprising a fiber optic means having distal and proximal ends, whereon the distal end is located adjacent said lens means and the projected lens image and which includes a series of optical fibers laterally aligned in a plane through an axis extending from the center of said lens means and the center of the fringe image.

9. A system for the simultaneous measurement of the size and velocity of particles within a multiphase process comprising:

(a) a source of light for generating a light beam;

(b) fringing means for projecting a fringe image of a series of parallel planes of alternating dark and light spaces in response to said light beam;

(c) imaging means having proximal and distal ends comprising a coherent fiber optic bundle for transmitting said fringe image from the proximal end of the imaging means to the distal end thereof;

(d) lens means at the distal end of the imaging means for projecting said fringe image into space;

(e) velocity and size sensor means comprising a pair of fiber optic means, each having a distal end located adjacent said lens means at an askew angle with respect to said lens means for sensing the light refracted or reflected from particles passing through the fringe image and for transmitting said reflected or refracted signal to the proximal end of said sensor means;

(f) light detector means coupled to the proximal end of said sensor means for converting the sensed light to an electrical signal proportional thereto; and (g) signal processing means for determining the velocity and size of said particles in response to said electrical signal by determining the phase lag between the light waves sensed by each fiber optic means.

* * * * *